United States Patent [19]

Towle

[11] Patent Number: 5,338,821

[45] Date of Patent: Aug. 16, 1994

[54] ARYL-ETHER-SULPHONE MONOMERS AND ARYL-ETHER-KEYTONE-SULFPHONE POLYMERS

[75] Inventor: Ian D. H. Towle, Cirencester, England

[73] Assignee: Raychem Limited, London, United Kingdom

[21] Appl. No.: 39,471

[22] PCT Filed: Oct. 23, 1991

[86] PCT No.: PCT/GB91/01858

§ 371 Date: Apr. 26, 1993

§ 102(e) Date: Apr. 26, 1993

[87] PCT Pub. No.: WO92/07843

PCT Pub. Date: May 14, 1992

[30] Foreign Application Priority Data

Oct. 26, 1990 [GB] United Kingdom ............ 9023365.1

[51] Int. Cl.$^5$ .................................... C08G 75/23
[52] U.S. Cl. .................................... 528/173; 528/174; 528/125; 549/46
[58] Field of Search ............ 528/173, 174, 125; 549/46

[56] References Cited

U.S. PATENT DOCUMENTS

| | | | |
|---|---|---|---|
| 3,083,201 | 3/1963 | Anderson | 549/46 |
| 3,775,368 | 1/1972 | Leslie et al. | 528/174 |
| 4,252,937 | 2/1981 | Marvel et al. | 528/126 |
| 4,709,007 | 11/1987 | Jansons et al. | 528/222 |
| 4,716,211 | 12/1987 | Clendinning et al. | 528/126 |
| 4,820,792 | 4/1989 | Towle | 528/173 |
| 4,879,366 | 11/1989 | Jansons et al. | 528/125 |
| 5,068,447 | 11/1991 | Gors et al. | 568/309 |
| 5,239,042 | 8/1993 | Fukawa et al. | 528/174 |

OTHER PUBLICATIONS

Derwent Abstract 54795C/31 (abstract of SU 694,491).
Chemical Abstracts 111:174914b (abstractof JP 01-74223).
Chemical Abstracts 114(8):63856b (abstract of JP 90-245,228).
Chemical Abstracts 112(6):36819u (abstract of JP 89-153,722).

*Primary Examiner*—John C. Bleutge
*Assistant Examiner*—Helen F. Lee
*Attorney, Agent, or Firm*—Herbert G. Burkard; Yuan Chao

[57] ABSTRACT

Benzofuran-ether-sulphone monomers of formula and ether ketone polymers derived therefrom of formula 7 Claims, No Drawings

ARYL-ETHER-SULPHONE MONOMERS AND ARYL-ETHER-KEYTONE-SULFPHONE POLYMERS

This invention relates to novel aryl-ether-sulphone monomers and to polymers and copolymers, preferably aryl-ether-ketone-sulphone (AEKS) polymers and copolymers, containing units derived from these monomers.

Monomers for making AEKS polymers are often difficult and expensive to produce. One aspect of the present invention provides a monomer which can be made from readily available starting materials by a simple one-step process.

The aspect accordingly provides a compound of formula

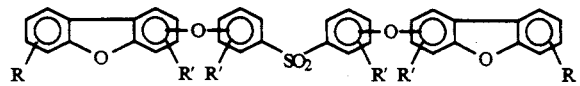

wherein each R independently is H, or $C_1$-$C_{10}$alkyl, and each R' independently is H. $C_1$-$C_{10}$ alkyl, or Cl or F, having at least one reactive hydrogen on each of the two end benzo-rings. Preferably, all the R groups will be H. Also preferably, the ether —O— groups will be in the para-position relative to the sulphone group and to the. furan oxygen. The most preferred monomer thus has the formula

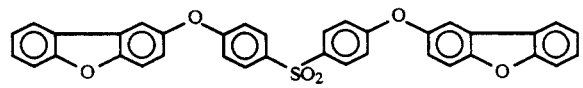

These aryl furan-ether-sulphone-ether-furan (FESEF) monomers may be prepared, for example by a method comprising reacting a dibenzofuran compound of formula

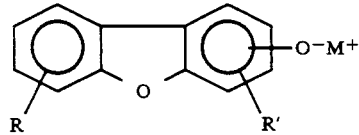

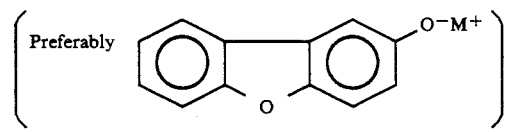

wherein M is an alkali metal, preferably Na, with a dihalide compound formula

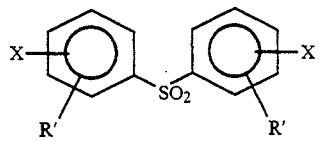

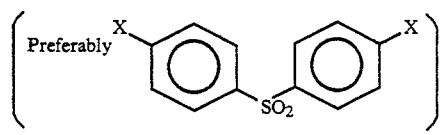

wherein X is halogen, preferably Cl, the molar ratio of the reacted dibenzofuran compound to the reacted dihalide compound being 2:1.

Appropriate starting materials, such as 2-hydroxydibenzofuran and 4,4'-dichlorodiphenylsulphone, are readily available in appropriately pure grades, and may for example be simply reacted by known procedures in the presence of alkali metal hydroxide (preferably sodium hydroxide) which produces the salt fore of the dibenzofuran for the above reaction.

The novel FESEF monomers may be used to produce polymers for example having a repeat unit of formula

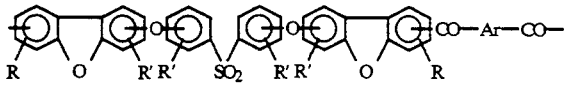

wherein R and R' are as defined above, and Ar is a mono- or poly-nuclear aromatic moiety in which two or more arylene groups if present may be linked by —CO—, —O—, —C(CH$_3$)$_2$—, —C(CF$_3$)$_2$—, or by a direct or fused-ring bond. Again it is preferred that all the groups are H and that the ether —O— groups are in the para positions, the most preferred polymers thus having the repeat unit

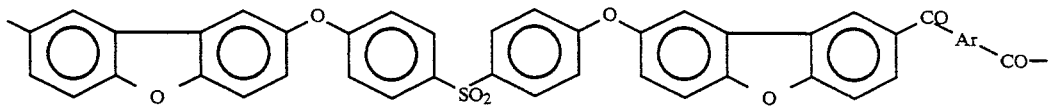

These FESEFKetone polymer units may be made by condensing a FESEF monomer as hereinbefore defined with a diacid halide, for example terephthaloyl chloride or isophthaloyl chloride, so that the FESEFKetone unit is the product of condensing a compound of formula

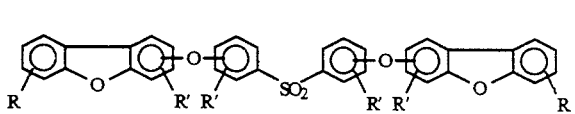

with a diacid halide compound of formula

X—CO—Ar—CO—X in the presence of a Lewis acid, preferably also in the presence of a Lewis base controlling agent for the Lewis acid.

The invention includes random or block copolymers of such FESEFKetone repeat units together with aryletherketone repeat units, preferably present in the form of a polymer pre-block, for example as described in our copending British Patent Application (RK419), the disclosure of which is incorporated herein by reference. Preferably, the copolymers will comprise 30 to 60 mol % of the aryletherketone repeat units, although higher and lower proportions thereof are not excluded. Suitable aryletherketone repeat units are described, for example in our published International Application WO90/00573, the disclosure of which is incorporated herein by reference.

The invention also provides a method of making the FESEFKetone polymers hereinbefore described comprising (A) reacting a compound of formula

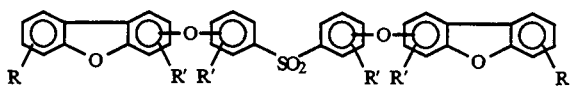

or a monomer, oligomer or polymer pre-block having two terminal moieties of formula (TT)

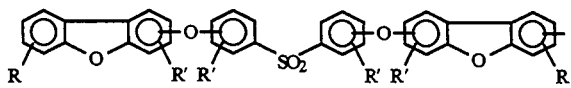

wherein each R independently is H, or $C_1$-$C_{10}$ alkyl, and each R' independently is H, $C_1$-$C_{10}$ alkyl, or Cl or F, having at least one reactive hydrogen on each of the two end benzo-rings, with a diacid halide component of formula

X—CO—Ar—CO—X or (B) self-reacting a monomer, oligomer, or polymer pre-block having one terminal moiety (TT) as above and one terminal acid halide group —COX, in the presence of a Lewis acid, preferably also in the presence of a Lewis base controlling agent for the Lewis acid.

Polymers could alternatively be made from acid halide-terminated derivatives of the compound (A) or terminal moieties (TT) with an arylene moiety having two active terminal hydrogens.

These preferred methods may be carried out according to the modified Friedel Crafts procedures generally described in our EP-A-0124276, using a catalytic molar excess of Lewis acid over the total Lewis base controlling agent and Lewis basic groups in the monomers; or according to an alternative procedure described in our copending British Patent Application 9010175.9 using a weak Lewis base as controlling agent in a molar amount which equals or exceeds the mount of Lewis acid, the latter being used in a molar amount which exceeds the amount of strongly Lewis basic species present. The disclosures of both of these references are incorporated herein by reference.

The following Example illustrates the use of a FESEF monomer, prepared by the aforementioned reaction from 2-hydroxydibenzofuran and 4,4'-dichlorodiphenylsulphone to form a block copolymer as described and defined in our copending British Patent Application (RK419), the disclosure of which is incorporated herein by reference.

The materials used were $AlCl_3$ as Lewis acid, dimethyl sulphone (DMS) as Lewis base, terephthaloyl chloride (TPC) 4,4'-diphenoxybenzophenone (DPB), the FESEF monomer, and 4-phenoxybenzophenone as end capper, in the following amounts, with dichloromethane as diluent:

|  | Reactant | mol | mass (g) |
|---|---|---|---|
| EK | $AlCl_3$ | 0.30550 | 40.7354 |
| BLOCK | DMS (Lewis base) | 0.08458 | 7.9618 |
|  | TPC (1st addition) | 0.02666 | 5.4133 |
|  | DPB | 0.03333 | 12.2140 |
| EKS | TPC (2nd addition) | 0.02973 | 6.0348 |
| BLOCK | FESEF monomer | 0.02222 | 12.9454 |
|  | End Capper | 0.00167 | 0.4572 |

Diluent=dichloromethane of which 50 ml was added at the start, with a further 20 ml used to wash m the reactants.

A reaction vessel fitted with a PTFE stirrer, thermocouple, and nitrogen inlet containing the required amount of dichloromethane diluent was pre-cooled to minus 13° C., and the required amount of aluminum chloride catalyst was added while stirring, keeping the temperature below −5° C., followed by the required amount of dimethylsulphone (Lewis base), which was added slowly, not allowing the temperature to rise above minus 5° C. The required molar quantity of DPB (previously referred to) was then added together with just enough TPC (previously referred to) to produce the EK block. The nitrogen was then turned off and a scrubber attached whilst the temperature was allowed slowly to reach 20° C. After ¾ of an hour the scrubber was replaced by the nitrogen inlet and the reaction vessel was cooled to below 0° C. The FESEF sulphone monomer was added in the required molar quantity together with sufficient additional TPC to form the copolymer and together with an appropriate amount of an end capper, 4-phenoxybenzophenone, as known per se. The temperature was then raised slowly to 20° C. and the copolymer gelled as the reaction progressed to completion over a period of about 5 hours. The copolymer gel was decomplexed by vigorous blending in iced water until white, after which it was filtered and washed in known manner. After stirring for more than 6 hours in distilled water, followed by boiling for 30 minutes, the polymer fluff produced was filtered and washed 3 times with distilled water followed by drying overnight at 125° C. The resulting block copolymer has glass transition temperature Tg (DSC)=194° C., fastest crystallization temperature Tc (DSC)=252° C., and melting temperature Tm (DSC)=363° C., measured by the well known method of DSC (Differential Scanning Calorimetry).

EXAMPLE 2

Preparation of

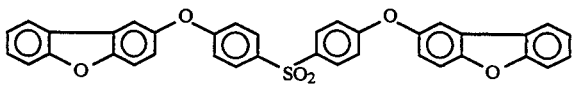

40 g (1 mol) of NaOH dissolved in 100 mls of distilled water was added to a 2 liter reaction vessel fitted with a mechanical stirrer, nitrogen inlet/outlet. Dean-Stark head and condenser. To the aqueous solution was then added to 1 liter of N-methyl-2-pyrolidinone (N.M.P.), 100 mls of toluene and 184 g (1 mol) 2-hydroxydibenzofuran. The reaction mixture was heated to boiling and the water removed by use of the Dean-Stark head. When all the water had been removed the reaction mixture was allowed to cool slightly, under a stream of dry nitrogen, 115 g (0.4 mol) of 4,4'-dichlorodiphenylsulphone was added to the anhydrous sodium salt of 2-hydroxydibenzofuran in the N.M.P. The reaction mixture was then heated to 200° C. for 4 hours. After this time the mixture was allowed to cool to room temperature. The crude product was precipitated by pouring the reaction mixture into 3 liters of methanol. The crude solid was filtered and re-slurried in deionised water in order to remove sodium chloride. After filtering, the crude product was again slurried in 2 liters of methanol and then filtered in order to remove the excess 2-hydroxydibenzofuran. After filtering, the crude solid was dissolved in 1 liter of chloroform and decolourised with charcoal (10 g). After removing the chloroform the product was crystallised from a mixture of methanol: 1.2-dichloromethane ( 1:1), giving a white crystalline product having a melting point of 161°–162° C. The purity as measured by DSC was found to be 99.23%. The yield was 70%, 163 g.

EXAMPLE 3

Preparation of the Homopolymer

To a 150 ml reaction flask fitted with a mechanical stirrer and nitrogen inlet/outlet was added 30 mls of anhydrous dichloromethane. After cooling the flask to −20° C., 10 g (0.075 mol) of anhydrous aluminium chloride was added. Having allowed the slurry to cool back to −20° C. 1.61 g (0.017 mol) of dimethylsulphone was added to the slurry keeping the temperature of the slurry below −10° C. Also at −20° C. 5 g (8.58×10⁻³ mol) of the dibenzofuran sulphone monomer from Example 2 was added to the reaction flask along with 1.74 g (8.58×10⁻³ mol) if terephthaloyl chloride. Last traces of these last two components were washed into the reaction vessel with a further 20 mls of anhydrous dichloromethane. The reaction was then allowed to warm, whilst stirring, to 20° C. During this time hydrogen chloride was evolved and slowly the reaction mixture thickened and eventually set. After 5 hours at 20° C. the polymer was decomplexed from the aluminium chloride by blending in a waring blender in iced water. The white polymer fluff was filtered off and slurried in deionised water at room temperature for 6 hours. After this time the slurry was heated to boiling for 1 hour after which the polymer fluff was filtered off and washed on the filter with 3×100 mls of deionised water. The polymer fluff was dried at 125° C. overnight.

The I.V. of the polymer was 1.54 dl/g measured as a 0.1% solution in sulphuric acid. The Tg of the polymer was 260° C.

EXAMPLE 4

Following the procedure outlined in Example 3 a random copolymer was prepared using the following reagents.

| FESEF | 2.2241 g | $3.8175 \times 10^{-3}$ mols |
| --- | --- | --- |
| 4,4'-diphenoxybenzophenone | 3.2639 g | $8.9075 \times 10^{-3}$ mols |
| 4-phenoxybenzophenone | 0.1969 g | $7.6308 \times 10^{-4}$ mols |
| terephthaloyl chloride | 2.6609 g | $1.3108 \times 10^{-2}$ mols |
| dimethyl sulphone | 2.162 g | $2.3 \times 10^{-2}$ mols |
| aluminium trichloride | 11.25 g | $8.437 \times 10^{-2}$ mols |
| dichloromethane | 75 mls | |

The I.V. of the resultant random copolymer was 0.73 dl/g.

The Tg of the random copolymer was at 193° C., as measured by DSC, and Tm of 348° C.

EXAMPLE 5

Following the procedure outlined in Example 3 a random copolymer was prepared using the following reagents.

| FESEF | 3 g | $5.1493 \times 10^{-3}$ mols |
| --- | --- | --- |
| 4,4'-diphenoxybenzophenone | 4.3963 g | 0.01199 mols |
| terephthaloyl chloride | 3.4812 g | 0.01714 mols |
| dimethyl sulphone | 3.2 g | 0.034 mols |
| aluminium trichloride | 16.5 g | 0.1237 mols |
| dichloromethane | 100 mls | |

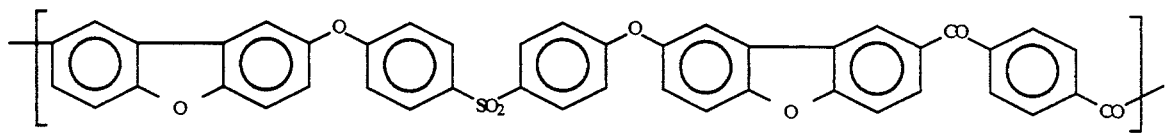

The I.V. of the resultant random copolymer was 1.94 dl/g.

The Tg of the random copolymer was 200° C.

I claim:

1. A polymer having a FESEFKetone repeat unit of formula

wherein each R independently is H, or $C_1$-$C_{10}$ alkyl, and each R' independently is H, $C_1$-$C_{10}$ alkyl, or Cl or F, and Ar is a mono- or poly-nuclear aromatic moiety in which two or more arylene groups if present may be linked by —CO—, —O—, —C(CH₃)₂—, —C(CF₃)₂—, or by a direct or fused-ring bond.

2. A polymer according to claim 1, wherein the FESEFKetone unit is the product of condensing a compound of formula

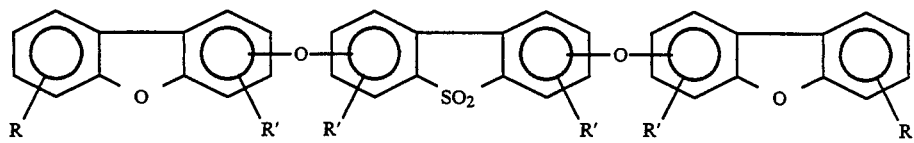

with a dihalide compound of the formula

X—CO—Ar—CO—X in the presence of a Lewis acid.

3. A random or block copolymer comprising FE-SEFKetone repeat units as defined in claim 1 together with aryletherketone repeat units.

4. A block copolymer according to claim 3 wherein at least the aryletherketone repeat units are present in the form of a polymer pre-block.

5. A copolymer according to claim 3 comprising 30 to 60 mol % of the aryletherketone repeat units.

6. A polymer according to claim 3, having a repeat unit of the formula

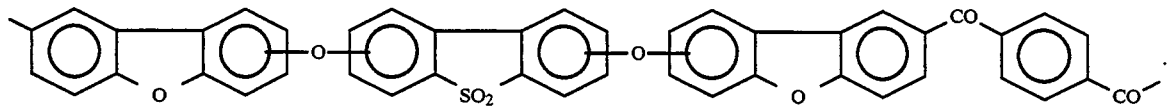

7. A polymer according to claim 5, which is a random copolymer.

* * * * *